US007977097B1

(12) United States Patent
Gay et al.

(10) Patent No.: US 7,977,097 B1
(45) Date of Patent: Jul. 12, 2011

(54) METHOD OF SCREENING MULTIPLY TRANSFORMED CELLS USING BICISTRONIC EXPRESSION OF FLUORESCENT PROTEINS

(75) Inventors: Robert D. Gay, Middlesex (GB); Noelle-Anne Sunstrom, New South Wales (AU); Peter Philip Gray, New South Wales (AU)

(73) Assignee: The University of New South Wales, Kensington (AU)

( * ) Notice: Subject to any disclaimer, the term of this patent is extended or adjusted under 35 U.S.C. 154(b) by 999 days.

(21) Appl. No.: 10/130,919

(22) PCT Filed: Nov. 24, 2000

(86) PCT No.: PCT/AU00/01436

§ 371 (c)(1),
(2), (4) Date: Mar. 11, 2003

(87) PCT Pub. No.: WO01/38557

PCT Pub. Date: May 31, 2001

(30) Foreign Application Priority Data

Nov. 24, 1999 (AU) .................................. PQ4223

(51) Int. Cl.
*C12P 21/04* (2006.01)
*C12P 1/00* (2006.01)
*C12N 15/00* (2006.01)

(52) U.S. Cl. ....... 435/455; 435/41; 435/71.1; 435/320.1

(58) Field of Classification Search ................ 435/41, 435/71.1, 320.1, 455
See application file for complete search history.

(56) References Cited

U.S. PATENT DOCUMENTS 5,610,034 A * 3/1997 Nyyssonen et al. ......... 435/69.6
5,968,738 A 10/1999 Anderson et al.
6,670,449 B1 * 12/2003 Miesenbock et al. ......... 530/350

OTHER PUBLICATIONS

Beavis et al (Cytometry, vol. 37: 68-73, 1999).*
Schultz et al (Journal of Virology, 1996, vol. 70, No. 2, pp. 1041-1049).*
Martinez-Salas et al (Current Opinion in Biotechnology 1999, vol. 10, pp. 458-464).*
Liu et al. (Biochemical and Biophysical Research Communications, 1999. vol. 260, pp. 712-717).*
Anderson, M.T. et al., Proc Natl Acad Sci USA (1996) 93 pages 8508-8511 "Simultaneous fluorescence-activiated cell sorter analysis of two distinct transcriptional elements within a single cell using engineered green fluorescent proteins".
Mosser, D.D. et al., Biotechniques (1997) 22(1) pp. 150-161, "Use of a dicistronic expression cassette encoding the green fluorescent protein for the screening and selection of cells expressing inducible gene products".
Welsh, S. et al, Curr Opin Biotechnol (1997) 8 pages 617-622, "Reporter gene expression for monitoring gene transfer" p. 617, col. 2, paragraph 2 and p. 618, col. 2, paragraph 1.
Zhu, J. et al, Cytometry (1999) 37(1) pp. 51-59, "Three-color flow cytometry analysis of tricistronic expression of eBFP, eGFP, and eYFP using EMCV-IRES linkages".

* cited by examiner

*Primary Examiner* — Peter Paras, Jr.
*Assistant Examiner* — David Montanari
(74) *Attorney, Agent, or Firm* — Ropes & Gray LLP; David P. Halstead

(57) ABSTRACT

A method of screening multiply transformed/transfected cells to identify those cells expressing at least two peptides or proteins of interest. The method comprising: 1. Simultaneously or sequentially transforming a cell with at least two different expression cassettes in which the gene of interest is linked via an IRES to a fluorescent marker gene. Each marker gene is different. 2. Providing conditions in which expression of the genes will occur. 3. Identifying cells expressing proteins by detecting the different fluorescent signals.

40 Claims, 8 Drawing Sheets

A

B

C

D

E

A

B  C

METHOD OF SCREENING MULTIPLY TRANSFORMED CELLS USING BICISTRONIC EXPRESSION OF FLUORESCENT PROTEINS

This application is a 35 USC 371 U.S. national phase entry application of International Application No. PCT/AU00/01436, filed Nov. 24, 2000, which claims priority from Australia Application No. PQ 4223 filed Nov. 24, 1999. The entire contents of the above-referenced patent applications are incorporated herein by reference. International Application No. PCT/AU00/01436 was published under PCT Article 21(2) in English.

TECHNICAL FIELD

The present invention relates to methods of screening transformed or transfected cells and in particular to a method of screening cells to identify those expressing at least two specific peptides and/or proteins of interest.

BACKGROUND

Techniques used to identify cells which have incorporated transfected DNA and which express the exogenous gene encoded by the transfected DNA are slow and often involve exposure of the cells to compounds which, as seen for example in biopharmaceutical production, are not always acceptable. Fluorescent proteins are well-known and it has previously been shown that incorporation of a gene that expresses a fluorescent protein into a transfected DNA species allows cells expressing the fluorescent protein to be identified by flow cytometry. It has also been shown that transfection of a DNA species in which a gene encoding a fluorescent protein is fused to a gene encoding a protein of interest, may be useful to localise the protein of interest in the transfected cells.

However, the difficulty of screening for cells expressing two or more proteins encoded by transfected DNA when the proteins are not fused to a fluorophore remains. The difficulties are further compounded when screening for expression of multi-subunit proteins.

It is an object of the present invention to overcome or ameliorate at least one of the disadvantages of the prior art, or to provide a useful alternative.

SUMMARY OF THE INVENTION

The present invention relates to a method of identifying and isolating those cells which have incorporated and expressed at least two exogenous DNA species encoding peptides or proteins of interest. The method involves the use of two differently coloured fluorescent proteins to track the expression of at least two peptides or proteins of interest when the peptides or proteins of interest are not fused to the fluorescent proteins. The technique may also be applied to the expression of multi-subunit proteins encoded by at least two separate sequences. The method is useful, for example, in antibody production. In the present expression system, one coloured fluorescent protein gene is expressed from the same promoter as the first protein of interest gene by coupling both sequences using a dicistronic (IRES) system. Likewise, a second coloured fluorescent protein gene is expressed from a second promoter coupled to the second gene of interest by a second IRES sequence. In this way, cells expressing the two expression cassettes may be identified and isolated using a fluorescence assisted cell sorter (FACS). Technical difficulties which were encountered and overcome are described.

According to a first aspect, the invention provides a method of screening transformed or transfected cells to identify those cells expressing simultaneously and/or sequentially at least two peptides or proteins of interest including:

(a) transformation or transfection of cells with at least two expression cassettes, wherein each expression cassette includes a gene encoding a peptide or a protein of interest linked at its 3' end to an internal ribosome entry sequence (IRES) wherein the IRES is linked at its 3' end to a fluorescent marker gene, such that the genes and their respective IRESs are in the same orientation, and wherein the detectable fluorescence of the products of the marker genes attached to each IRES are different;

(b) provision of conditions wherein expression of the genes encoding the peptides or proteins of interest occurs and wherein expression of the genes of interest results in expression of the fluorescent marker genes; and (c) identification of cells expressing at least two peptides or proteins of interest by detecting fluorescent signals from the products of the marker genes in the transformed or transfected cells using a fluorescence detection means.

It will be clear to the skilled addressee that more than two expression cassettes may be transformed or transfected into the cells.

Preferably, the cells identified on the basis of their expression of the fluorescent marker genes are selected and isolated from the other cells and, preferably, the isolated cells are cultured and/or subjected to further selection procedures.

The skilled addressee will understand that the transformation or transfection of the expression cassettes may be performed simultaneously or sequentially.

Most preferably, the fluorescent marker genes encode enhanced green fluorescent protein (EGFP) or enhanced yellow fluorescent protein (EYFP). However, it will be recognised by those skilled in the art that genes encoding any protein that can be detected by a fluorescence detection means will be suitable, including genes encoding green fluorescent protein (GFP) or a derivative of GFP the fluorescence of which is shifted towards the red or blue/violet part of the spectrum, eg enhanced yellow fluorescent protein (EYFP), blue fluorescent protein (BFP), enhanced blue florescent protein (EBFP), enhanced cyan fluorescent protein (ECFP) and the like. Alternatively fluorescent proteins, and their derivatives, obtained from other sources may be used. For example dsRed, derived from the IndoPacific sea anemone relative Discosoma striata, could be used. Preferably, the detection means is a fluorescence assisted cell sorter (FACS). Preferably, cells expressing at least two peptides or proteins of interest are gated and isolated from others. However, other fluorescent detection systems could also be used to identify dual fluorescent cells. Such systems include fluorescent plate readers or laser scanning cytometers which may be useful in identifying pools of cells with elevated levels of dual or multiple fluorescence or individual cells after limiting dilution. A microscope designed to allow visualisation of fluorescent cells may also be used.

In one embodiment of the invention, at least one of the fluorescent signals is attenuated. The attenuation may be achieved by genetic, electrical or optical means or by any other suitable means. In one embodiment, the signal attenuation by genetic means is achieved by use of an attenuated IRES sequence. An attenuated IRES will allow for diminished production of the marker gene product relative to production of the protein of interest. Thus, cells expressing high levels of the peptide or protein of interest, particularly of a subunit of a protein of interest, are selected.

In another embodiment, the signal attenuation by electrical means is achieved by manipulation of the fluorescence detection means. For example, electrical attenuation may be performed by altering the settings on a fluorescence assisted cell sorter (FACS) for the respective photomultiplier tubes (PMT1, PMT2 etc) or by altering the alignment of the fluorescence detectors (FL1, FL2 etc). Such manipulations would be well within the capacity of those skilled in the operation of a flow cytometer.

In still a further embodiment, the signal attenuation by optical means is achieved by manipulating the filters placed between the fluorescing cells and the fluorescence detector and in another embodiment, the signal attenuation by optical means is achieved by placing a neutral density 2 filter in front of an FL1 detector to obtain a reduction of about 2 log decades in the intensity of fluorescence.

The genes encoding the peptides or proteins of interest may be genes encoding peptides which are subunits of a single protein. Preferably, the peptides of interest are the heavy and light chains of an antibody. However, the skilled addressee will recognise that the method may be used to identify any cells in which expression of two or more related peptides or proteins of interest is required (eg. expression of FSH Follicle Stimulating Hormone), or in which dual expression of genetically and functionally unrelated proteins is required (eg. expression of Insulin-like Growth Factor I (IGF-1) and transferrin in the Super-CHO™ cell line (Pak et al 1996)).

Preferably, at least two of the peptides or proteins of interest are expressed in a ratio of about 1:1. However, it will be clear to the skilled addressee that other ratios are also contemplated and that cells expressing high levels of the peptide or protein of interest encoded by one cassette but lower levels of the peptide or protein encoded by another cassette may also be selected with the appropriate fluorescence detection equipment.

In one embodiment, at least one of the peptides is a limiting subunit of a bi- or multi-unit molecule. In a further embodiment, the limiting subunit is expressed at equivalent or higher levels than one or more of the other peptides of interest. Preferably, at least one of the expression cassettes further includes a gene allowing selection in growth medium. More preferably, the gene allowing selection in growth medium is a gene encoding metal resistance or a gene encoding resistance to an antibiotic. More preferably, the metal resistance is resistance to cadmium and/or zinc and most preferably, the gene encoding metal resistance is the human metallothionein gene. Alternatively the expression cassette may be present in amplifiable gene expression vectors, such as those used in the DHFR and GS systems.

Preferably, the gene encoding antibiotic resistance it a gene encoding resistance to geneticin (G418).

In a preferred embodiment, at least one of the expression cassettes is under metal inducible control. Preferably, the metal inducible control is achieved by means of the M2.6 promoter.

In one embodiment, at least one of the expression cassettes is a linear fragment of DNA.

In another embodiment, at least two of the expression cassettes are on the same DNA fragment.

Preferably, at least one of the expression cassettes is included in a vector. It will be clear to the skilled addressee that the vector may be any suitable vector including an episomal plasmid. In one embodiment, at least one of the expression cassettes is integrated into the cell's genomic DNA.

Preferably, the cells transformed or transfected are mammalian cells, more preferably, they are chinese hamster ovary (CHO) cells and most preferably, they are CHO-K1 cells. However, the skilled addressee will understand that any suitable cells may be used.

In one embodiment, the cells transiently express at least one of the peptides or proteins of interest. However, it will be clear to the skilled addressee that the cells may also stably express at least one of the peptides or proteins of interest.

Preferably, the cells are identified after 2 to 40 days' incubation post transformation or tranfection. More preferably, the cells are identified after about 28 days selection in selective growth medium and, most preferably, the cells are identified after about 14 days selection in a first selective growth medium and about 14 days selection in a second selective growth medium. Preferably, the first selective growth medium includes geneticin to select for cells having geneticin resistance and the second growth medium includes metal salts to select for cells having a gene encoding metal resistance, the genes encoding resistance are on the expression cassettes.

For example, when identifying cells transiently expressing the proteins or peptides of interest, cell populations may be analysed after about 2 days' incubation. It will be clear to the skilled addressee that, when transient expression of the proteins or peptides of interest is analysed, electrical and/or optical attenuation may be more appropriate than genetic attenuation. When cells stably expressing the peptides or proteins of interest are required, first and second FACS analysis steps may be performed at appropriate intervals.

According to a second aspect, the invention provides cells identified by a method according to the invention.

According to a third aspect, the invention provides an expression product derived from cells screened by a method according to the invention.

According to a fourth aspect, the invention provides an expression system including a cell identified by a method according to the invention.

According to a fifth aspect, the invention provides a kit including at least one expression cassette including a gene encoding a peptide or protein of interest linked at its 3' end to an attenuated IRES, wherein the attenuated IRES is linked at its 3' end to a fluorescent marker gene, such that the gene and the IRES are in the same orientation when used in a method according to any one of claims 1 to 40 optionally including instructions for use.

According to a seventh aspect, the invention provides expression cassettes when used in a method according to the invention.

According to an eighth aspect, the invention provides a protein of interest when identified and/or isolated by a method including a method according to the invention. Preferably, the protein of interest is an antibody and, most preferably, it is c30.6 chimeric mouse antibody.

According to a ninth aspect, the invention provides a method of producing a peptide or protein of interest which includes identification of cells producing the peptide or protein by a method according to the invention.

According to a tenth aspect, the invention provides a method of producing a protein of interest consisting of at least two subunits including:

(a) transforming or transfecting cells with at least two expression cassettes either simultaneously or sequentially wherein (i) at least one expression cassette has a first gene encoding a first subunit of the protein of interest linked at its 3' end to a first internal ribosomal entry sequence (IRES) wherein the first IRES is linked at its 3' end to a first fluorescent marker gene, such that the first gene, the first IRES and the first fluorescent marker gene are in the same orientation; and (ii) at least one other expression cassette has a second gene encoding a second subunit of the protein of interest linked at its 3' end to a second internal ribosomal entry sequence (IRES) wherein the second IRES is linked at its 3' end to a second fluorescent marker gene, such that the second gene, the second IRES and the second fluorescent marker are in the same orientation; and wherein expression of the genes encoding the subunits results in expression of the fluorescent marker genes; and (b) screening the transformed or transfected cells to identify cells expressing the subunits of the protein of interest by detecting fluorescent signals from the transformed or transfected cells using fluorescence detection means.

(c) isolating the identified cells expressing the subunits;

(d) optionally enriching the identified cells by further selection;

(e) isolating the protein of interest from the identified cells.

Preferably, the first and second genes are genes encoding the heavy and light chains of an antibody respectively and more preferably, the antibody is c30.6 chimeric mouse antibody.

According to an eleventh aspect, the invention provides a method of screening transformed or transfected cells to identify those cells expressing simultaneously and/or sequentially at least two peptides or proteins of interest including:

(a) transformation or transfection of cells with a first expression cassette including a gene encoding one peptide or protein of interest linked at its 3' end to an attenuated IRES, the attenuated IRES being linked at its 3' end to an enhanced green fluorescent protein (EGFP) marker gene, wherein the gene encoding the peptide or protein of interest, the attenuated IRES and the EGFP marker gene are in the same orientation;

(b) transformation of the same cells with a second expression cassette including a gene encoding one peptide or protein of interest linked at its 3' end to attenuated IRES, the IRES being linked at its 3' end to an enhanced yellow fluorescent protein (EYFP) marker gene, wherein the gene encoding the peptide or protein of interest, the attenuated IRES and the EYFP marker gene are in the same orientation;

(c) provision of conditions in which expression of the genes encoding the peptides or proteins of interest occurs and wherein expression of the genes of interest results in expression of the EGFP and EYFP marker genes; and (d) identification of cells expressing at least two peptides or proteins of interest by detecting the presence of EGFP and EYFP in the transformed or transfected cells using FACS analysis.

DESCRIPTION OF THE INVENTION

Figure 1:
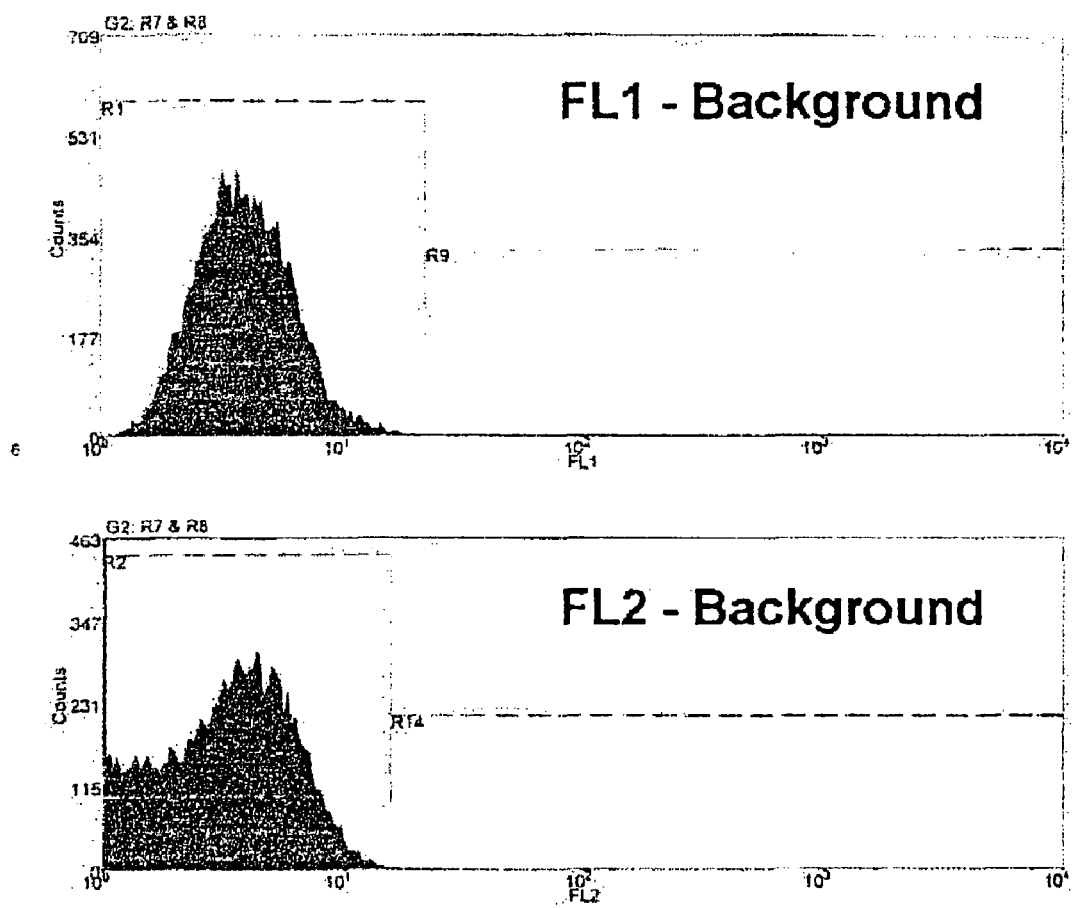
FIG. 1: Histograms of background fluorescence of untransfected CHO-K1 cells. Top histogram shows the FL1 channel from the FACS machine (x-axis=FL1/Green fluorescence: y-axis=Number of cells). Bottom histogram shows the FL2 channel from the FACS machine x-axis=FL2/Yellow fluorescence: y-axis=Number of cells).

The green fluorescent protein (GFP) was originally identified in the jelly fish *Aeqourea victoria* from which the gene was later cloned (Chalfie, M. et al. 1994; WO 95/07463). This protein which fluoresces bright green when exposed to ultra violet or blue light, requires no substrates or co-factors and functions in vivo with little deleterious effects on host cells. Although GFP only fluoresces weakly, optimized variants have been produced which emit fluorescence at brighter intensities and at different colour wavelengths. The Enhanced Green Fluorescent Protein (EGFP) (also known as GFPmut1; U.S. Pat. No. 5,804,387) has been used in these experiments to exemplify the invention. The EGFP sequence includes some 190 silent base pair mutations, which correspond to human codon-usage preferences, fluoresces some 35 times stronger than the wild type GFP (Hass J. et al 1996). The EGFP protein also exhibits a single red-shifted excitation peak with a 488 nm maximum.

A similar excitation profile is exhibited by the Enhanced Yellow Fluorescent Protein (EYFP; also known as GFP-10C; U.S. Pat. Nos. 5,625,048 and 5,777,079) which has also been used to exemplify the present invention. EYFP also contains mutations that shift the emission wavelength from green (EGFP max=507 nm) to yellowish-green (EYFP max=527 nm) (Ormo, M. et al. 1996). These factors make EGFP and EYFP useful for excitation and detection using a Fluorescence Assisted Cell Sorter (FACS) equipped with a single 488 nm argon-ion laser. The application of a selected set of commercially available filters to the FACS machine allows cells expressing EGFP, EYFP or both to be screened and sorted (see FIG. 1). The skilled addressee will recognise that the use of two lasers (one, for example, at 458 nm and one, for example, at 514 nm) could also be used for EGFP/EYFP detection. Other fluorescent proteins will require other laser specification.

Although EGFP and EYFP fluoresce at similar intensities and may be excited by the same light source, other variant combinations of GFP, even with greatly different excitation profiles may also be utilised in tracking the expression of two proteins. The skilled addressee will recognise that any fluorescent proteins may be used including any fluorescent protein derived from GFP which is red or violet shifted from the original green and those derived from another source, such as *Dicosoma striata*. For example, Enhanced Blue Fluorescent Protein (EBFP–excitation=380 nm emission=440 nm) (Yang et al 1998), Enhanced Cyan Fluorescent Protein (ECFP–excitation=433 and 453 nm, emission=475 and 501 nm) may be useful in the present invention. Any two or more fluorescent protein combinations may be used and applied to FACS analysis to allow the identification of transfected cells expressing the expression cassettes. By applying the attenuation means indicated, the present invention may be used for screening and isolating from a cell population those cells expressing, for example, both high levels of fluorescent colour one and fluorescent colour two, and consequently, as a result of the dicistronic nature of each gene expression cassette, those cells expressing high levels of the peptides or proteins of interest.

The Internal Ribosomal Entry Sequence (IRES)

In order to ensure that cells expressing a specific fluorescent protein also express a particular protein of interest the open reading frames (ORF) for both genes are arranged around an IRES sequence in such a way which ensures both genes are transcribed simultaneously from the same promoter. These DNA sequences which may, for example, be derived from the encephalomyocaritis member of the Picornaviridae family of viruses provide a second entry site for ribosomes along the transcribed mRNA molecule. The following is a list of alternative sources of IRES sequences:

Picornavirus family
  Poliovirus subfamily
    Enterovirus
    Poliovirus
    Rhinovirus
  Cardiovirus subfamily
    Aphthovirus
    Cardiovirus
    Encephalomyocarditis
    Foot and Mouth Disease virus
Avian Reticuloendotheliosis virus type A
Hepatitis A virus
Hepatitis C virus
PDGF2/c-sis mRNA leader
Proto-oncogene c-myc
5' non-coding region of immunoglobulin heavy chain binding protein (BiP)
*Antenapedia* and *Ultrabithorax* genes of *Drosophila*
Mouse Fgf2 gene IRES sequences and their uses are described in Mountford & Smith (1995) and Martinez-Salas (1999).

Figure 2:
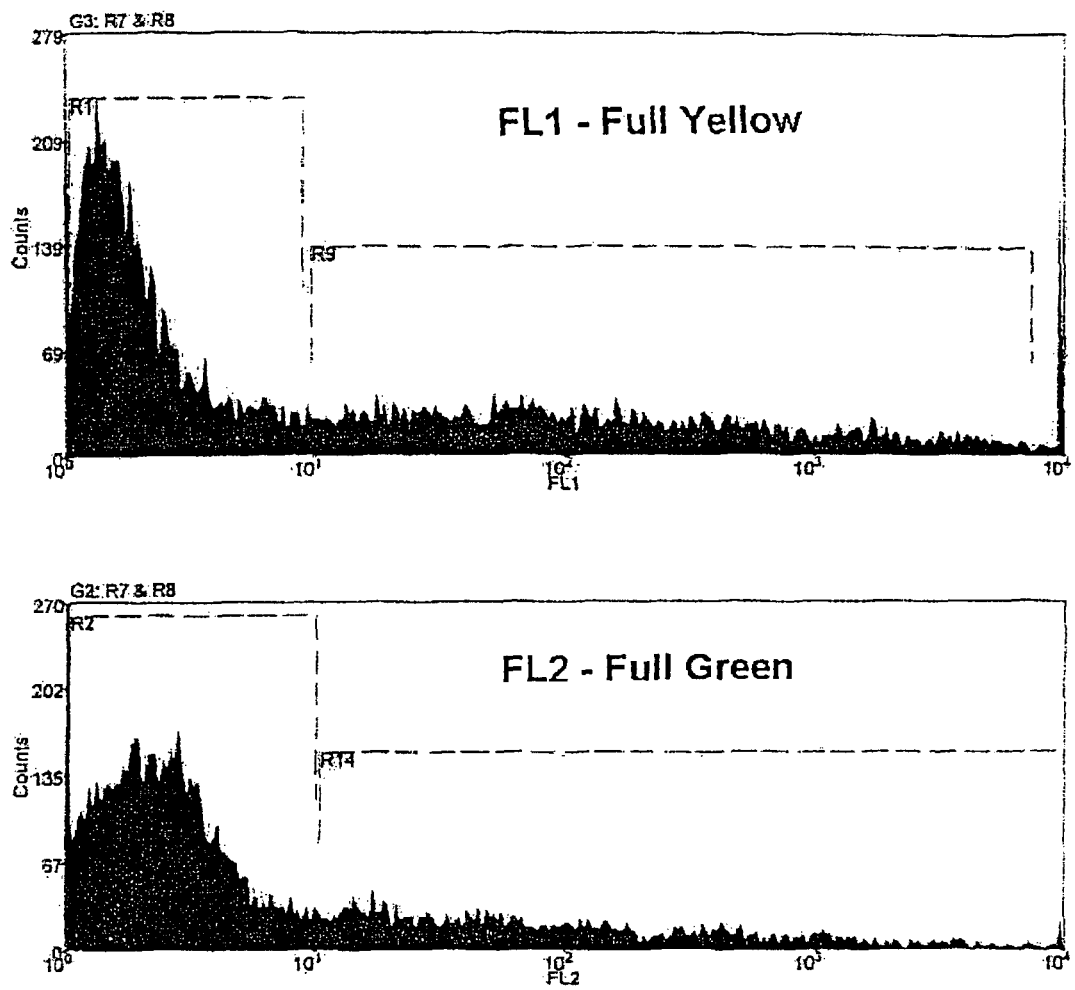
FIG. 2: Histograms of fluorescence of stably transfected CHO-K1 cells. Top histogram shows the FL1 channel from the FACS machine when cells are transfected with pEGFP-C1 (x-axis=FL1/Green fluorescence: y-axis=Number of cells). Bottom histogram shows the FL2 channel from the FACS machine when cells are transfected with pEYFP-C1 (x-axis=FL2/Yellow fluorescence: y-axis=Number of cells).

Thus the ORF for the gene upstream of the IRES sequence is translated by ribosomes which mount the mRNA at the 5' cap end, whilst the IRES sequence, which itself forms a 3 dimensional secondary structure within the mRNA, guides other ribosomes to mount the in RNA and translate the downstream gene (see FIG. 2).

In order to ensure that cells selected for the expression of fluorescence express high levels of the peptide or protein of interest, an attenuated IRES sequence may be used. By manipulation of the IRES DNA sequence the frequency of translation initiation events from the downstream ORF can be greatly reduced in favour of translation initiation events at the upstream ORF (Rees, S. et al 1996). As a result, any cells which are shown to express fluorescence will by default express higher levels of the protein whose gene is linked to the fluorescence gene via the attenuated IRES sequence. By selecting cells which express a given fluorescent colour at a chosen intensity and those which express the second fluorescent colour at a different intensity, the levels of expression of each of the two peptides of interest may be manipulated.

FACS Analysis and Sorting

The power of the FACS lies in its ability to screen large numbers of cells individually at rates of up to $1 \times 10^7$ cells per hour. Combined with powerful computer software, the FACS is able to identify groups of cells, a technique known as gating, and rapidly sort according to levels of fluorescence. Since cell sorting using the FACS machine may be performed in a sterile manner, those cells expressing high levels of the chosen fluorescent proteins may be returned to tissue culture flasks and maintained.

Using these techniques those cells which have incorporated exogenous DNA may be rapidly identified by screening and sorting for fluorescent protein expression following transfection. Whilst sorting within 48 hours of the transfection may yield cells only transiently expressing the fluorescent marker gene, a second sort after about 14 days should be sufficient to identify and isolate only those cells stably expressing the exogenous DNA.

Example 1

Preparation of DNA

Transfection quality DNA was produced using standard preparation techniques. Double cesium chloride, PEG precipitation or anion exchange columns may be used for preparation of such DNA. The method described here details the preparation of 25 ml *E. Coli* DH5α cultures for extraction of approximately 100 µg of transfection quality plasmid DNA using QIAFilter Midiprep anion exchange columns (Qiagen, Germany). Thus, fresh kanamycin (50 µg/ml) LB agar plates were streaked with glycerol stocks of *E. Coli* DH5α containing two pNK derived expression vectors (pNK-c30.6γ-IRES-EGFP and pNK-c30.6κ-IRES-EYFP). The pNK vectors used as the "backbone" in these examples of the dual expression system have recently been described (Bailey et al. 1999).

The pNK vector includes a multiple cloning site into which an antibody gene-IRES-fluorescent protein expression cassette was cloned (between ClaI and BclI restriction sites). Two vectors each including a different expression cassette were used. To exemplify the present invention, genes encoding the light and heavy chains of the c30.6 chimeric mouse antibody (Mount et al. 1994) were inserted into the vectors as described below. However, it will be clear to the skilled addressee that genes encoding any appropriate antibody sequences may be used as well as genes encoding the subunits of a multi-subunit protein.

Thus the Light Antibody chain-IRES-EYFP expression cassette was created by cloning sequences for the light antibody chain (see below) between the ClaI and EcoRI sites found in the multiple cloning site of the Clontech vector pIRES-EYFP. Once the antibody sequence was cloned in, the entire cassette was removed using ClaI and BclI, and inserted into the pNK backbone. This vector was named pNK-c30.6κ-IRES-EYFP.

The Heavy Antibody chain-IRES-EGFP expression cassette was created in a similar fashion except that the pIRES-EYFP vector was modified by removing the EYFP gene (AgeI-BclI digest) and replacing it with the EGFP gene (AgeI-BclI digest fragment) from the Clontech pEGFP-C1 vector. Once the antibody heavy chain sequence was inserted into this modified vector it was then cloned into the pNK backbone as described above. This vector was named pNK-c30.6γ-IRES-EGFP.

The antibody sequences used in the present example include the following:

1) Leader sequence to ensure secretion of produced protein;
2) Variable region sequence—light or heavy chain—mouse chimeric or human origin;
3) Human constant region sequence—light or heavy chain; and
4) A stop codon.

The sequences used in this invention must allow for the production of a continuous transcript from the gene encoding the peptide or protein of interest through the IRES and into the fluorescent protein gene. In the present example, in order to ensure that this could occur the gene encoding the antibody did not include any transcriptional termination sequences or signals.

After overnight incubation at 37° C. a single colony was selected from each plate and used to inoculate two 5 ml LB with kanamycin (50 µg/ml) cultures. These cultures were grown for 8 hours at 37° C. with 300 rpm shaking. Finally, 50 µl of each culture was used to inoculate two 25 ml LB with kanamycin (50 µg/ml) cultures for overnight incubation at 37° C. with 300 rpm shaking. Following overnight incubation, DNA was extracted following the QIAfilter protocol. Briefly, the overnight cell culture was pelleted at 6000×g for 5 minutes and then resuspended and mixed in Qiagen buffers P1, P2 and P3 resulting in a cell lysate. This lysate was then cleared using a QIAfilter cartridge and applied to an equilibrated QIAGEN-tip containing the anionic resin. The plasmid DNA was sequentially bound, washed and eluted from this resin and then precipitated in 0.7 volumes of isopropanol and washed with 70% ethanol. This resulted in approximately 100 µg highly super-coiled, transfection quality DNA.

Following the isolation and purification of transfection quality DNA, the vectors may be linearised before transfection. The pNK vectors have a unique MluI restriction enzyme site which may be cut without compromising the function of any of the required gene regions. Thus 20 µg of each DNA was linearised using 20 units of MluI by digestion for 90 minutes in the appropriate buffer. Following linearisation the DNA was again purified by extraction with a 1:1 mix of phenol:chloroform followed by precipitation in one tenth volume of 3M sodium acetate and 2 volumes of 100% ethanol, centrifugation at 13,000×g and washing in 70% ethanol. Following a final centrifugation at 13.000×g, the pelleted DNA was dried in a laminar flow hood before being resuspended in 20 µl Tris EDTA (pH 8) ready for transfection. At this point a 1 aliquot (equivalent to 1 µg) may be removed for analysis by resolving through a 0.8% agarose gel.

Those skilled in the art will recognise that the transfection of two (or more) DNA species which contain homologous sequences, such as the IRES (or attenuated IRES), fluorescent protein and vector sequence, could be expected to homologously recombine to form species which are not useful. However, the present invention shows that these events, if they did occur, did not prevent the proper functioning of the screening method.

The vectors described may be further modified to improve the efficiency of selection using G418 and metal following transfection:

For example: the human metallothionein II gene may be removed from one of the vectors. pNK-c30.6γ-IRES-EGFP was modified in this way and was renamed pKN-c30.6γ-IRES-EGFP.

The neomycin/kanamycin resistance gene may be removed and replaced with sequences for ampicillin resistance. Thus pNK-c30.6κ-IRES-EYFP has been modified in this way and has been renamed pMA-c30.6κ-IRES-EYFP.

These modified vectors, pKN-c30.6γ-IRES-EGFP and pMA-c30.6κ-IRES-EYFP, are both of a similar size (7338 bp and 7531 bp) which may promote equal uptake during transfection.

It will be clear to the skilled addressee that other combinations of these vectors are possible.

In the experiments described to exemplify the invention, we have elected to use the pNK vector backbone to construct the expression vectors for the following reasons:

(a) it is possible to establish stable incorporation of the two vectors into the genome of the transfected cells using G418 (Geneticin) selection;
(b) the expression cassette is under metal inducible control of the M2.6 promoter (McNeall et al, 1989);
(c) the presence of the human metallothionein gene, under the correct conditions, allows amplification of gene copy number and thus gene expression (Bailey et al 1999). This is a very useful characteristic of the vectors and is useful in this invention for increased expression of both first and second cistron genes. Coupled with the attenuation of the fluorescent proteins the skilled addressee will recognise the advantage that this provides, ie greatly increased expression of the first cistron gene coupled with increased expression of the second cistron gene which remains on scale when analysed with FACS.

Example 2

Transfection of DNA

Transfection of plasmid DNA into cells may be performed by many methods, including $CaPO_4$ precipitation, lipofection, electroporation and others. The following describes the use of Lipofectamine 2000 (a commercially available lipid derived system—GibcoBRL) which has provided good frequencies of transfection in attached and suspension CHO cells. The use of DMRIE C reagent (GibcoBRL) for high transfection efficiency where transfection of suspension cells is performed is also described.

For transfection using Lipofectamine 2000 (LF2000): The day before transfection $2 \times 10^5$ CHO-K1 cells were plated in wells of a 6 well plate with 2.5 ml of culture media with 10% fetal calf serum (e.g. DMEM:Coons F12 [a 1:1 mix]). As a result cells were 90-95% confluent on the day of transfection. 4 to 5 µg of DNA was diluted into 250 µl of serum free medium (e.g. Opti-MEM 1 media-Gibco BRL). 12 to 15 µl LF2000 was also diluted into another 250 µl of serum free medium and incubated at room temperature for 5 minutes. Both the diluted DNA and LF2000 were then mixed and incubated for 20 minutes at room temperature. This mix was then added directly to the wells and gently rocked to spread the mixture over the cells. This mixture is non-toxic to the cells and was therefore not removed from the media at a later point.

Alternatively, a CHO-K1 derived suspension cell-line (XL99) may be used which grows in a fully defined serum free medium (Ex Cell 302-JRH Biosciences). 3.5 µg of vector DNA is diluted into 200 µl of Opti-MEMI reduced serum medium whilst 12 µl of LF2000 is diluted into a further 200 µl of Opti-MEMI and incubated at RT for 5 minutes. Then the diluted DNA and LF2000 are mixed and incubated at RT for 20 minutes. XL99 cells are grown in Ex Cell 302 media until between 1 and $1.5 \times 10^6$ cells per ml. Cells are counted, pelleted and washed in 1×PBS, then resuspended in Opti-MEMI at $1.2 \times 10^6$ cells per ml. 2 ml of cells are aliquoted into a well of an untreated tissue culture dish and the DNA-LF2000 mixture is added. Cells are incubated at 37° C. with 5% $CO_2$ with gentle shaking. After 24 hours the cells are pelleted and the Opti-MEMI media is replaced with Ex Cell 302.

For transfection using DMRIE-C: On the day of transfection, 500 µl of serum free media was mixed with 4 µg DNA. 500 µl of serum free media was also aliquoted into wells of a 6 well plate. 2 to 12 µl DMRIE-C reagent was then added and the plate rocked gently to mix. The diluted DNA was then added and incubated at room temperature for 30 minutes. $2 \times 10^6$ cells were then added in a 200 µl volume and mixed in gently. Following a 5 hour incubation at 37° C., 2 ml of growth media with 10% FCS was added.

Example 3

Selection of Cells Transfected with DNA

In the case of attached CHO cells, 24 hours post transfection cells were detached in 500 µl 1:1 trypsin:versene solution, pelleted and resuspended in 500 µl growth media and inoculated into a large volume tissue culture flask (T75 or T150) in the presence of suitable media.

Suspension cells may also be used and may be cultured in T25 or T75 flasks which are untreated for tissue culture. When suspension cells were used, the flasks were shaken on an orbital platform at approximately 125 rpm. Suspension cells were also pelleted, resuspended and transferred to culture in 100 ml spinner bottles in the presence of suitable media.

After a further 24 hours, attached cells were selected with 500 µg/ml G418 (Geneticin) and/or 100 µM $Zn^{2+}SO_4^{2-}$ and 2 µM $Cd^{2+}Cl_2^-$ while the suspension cells are more sensitive due to the absence of serum and are therefore selected in 250 µg/ml G418. Selection was continued for 14 days with media and supplement replacement every 3 to 4 days. If attached cultures became greater than 80% confluent cells were passaged into larger culture vessels.

After 14 days, attached cells were detached in 1×PBS: EDTA solution, pelleted and resuspended in 2 ml growth medium and filtered through a 40 micron filter mesh before FACS analysis. Suspension cells were also filtered before FACS analysis.

Example 4

FACS Analysis

Cells were sorted to identify those expressing both EGFP and EYFP using a MoFlo fluorescence assisted cell sorter (FACS) with the Cyclops operating system. However, other FACS machines may also be used with the correct configuration. Following excitation of cells with a 488-nm argon laser, the application of one mirror and two filters allows the fluorescent signals to be differentiated. The additional hardware required consists of a 525-nm short pass dichroic mirror to separate the green and yellow fluorescent signals. The presence of this mirror allows the primarily EGFP fluorescence (below 525-nm) to enter photo multiplier tube 2 or 3 (PMT2 or 3) and be analysed as fluorescence 2 or 3 [FL2 or 3]) whilst the primarily EYFP fluorescence (above 525-nm) is reflected into photo multiplier tube 1 (PMT1) and is analysed as fluorescence 1 [FL1]). To further refine the fluorescence collected by each PMT a 510/20-nm bandpass filter was applied to PMT2 or 3—ensuring a green only signal—whilst a 550/30-nm bandpass filter was applied to PMT1—ensuring a yellow only signal.

Detection of Both Green and Yellow Fluorescence

Figure 3:
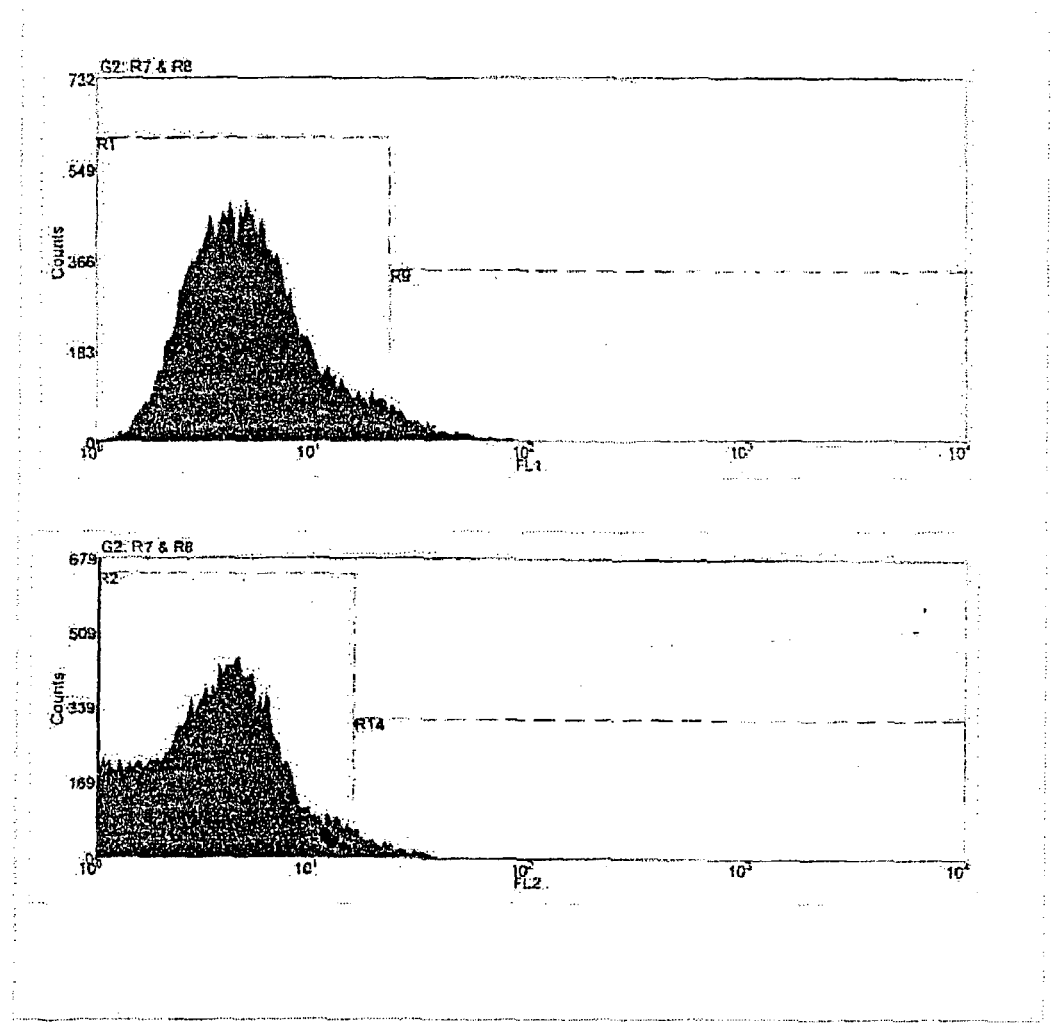
FIG. 3: Histograms of attenuated fluorescence of co-transfected CHO-K1 cells. Top histogram shows the FL1 channel from the FACS machine (x-axis=FL1/Green fluorescence: y-axis=Number of cells) and the bottom histogram shows the FL2 channel from the FACS machine (x-axis=FL2/Yellow fluorescence: y-axis=Number of cells) when cells are transfected with pNK-c30.6γ-IRES-EGFP and pNK-c30.6κ-IRES-EYFP.

FIG. 1 shows the background fluorescence for both FL1 and FL2 detected by the FACS machine for untransfected CHO-K1 cells. FIG. 2 shows the effect of transfecting CHO-K1 cells with the Clontech vectors pEYFP-C1 (FL1—top graph) and pEGFP-C1 (FL2—bottom graph). The design of the pNK constructs incorporates an IRES sequence which is attenuated, such that the second cistron is expressed at lower levels. As a result, the level of fluorescence obtained from CHO-K1 cells transfected with the pNK vectors is lower than could be expected in cells transformed with a vector in which the IRES had not been attenuated. FIG. 3 shows CHO-K1 cells co-transfected with pNK-c30.6κ-IRES-EYFP (FL1—top graph) and pNK-c30.6γ-IRES-EGFP (FL2—bottom graph). Although the second cistron is poorly expressed the first cistron will be expressed at high levels. Thus, identifying those cells expressing protein from the second cistron is a powerful method of identifying those cells expressing high levels of protein from the first cistron.

Differentiation Between Green and Yellow Fluorescence

Figure 4:
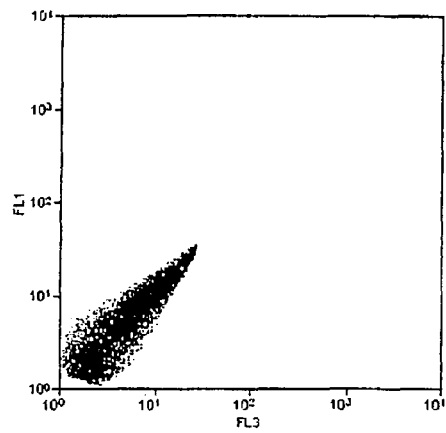
FIG. 4: FACS profiles. A: untransfected CHO cells; B: CHO cells transfected with pEGFP-C1; C: CHO cells transfected with pEYFP-C1; D: mixture of cells from B and C; E: Co-transfections of CHO cells using pEGFP-C1 and pEYFP-C1.
Figure 4:
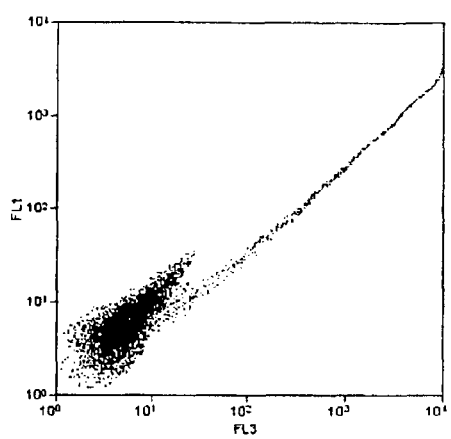
Figure 4:
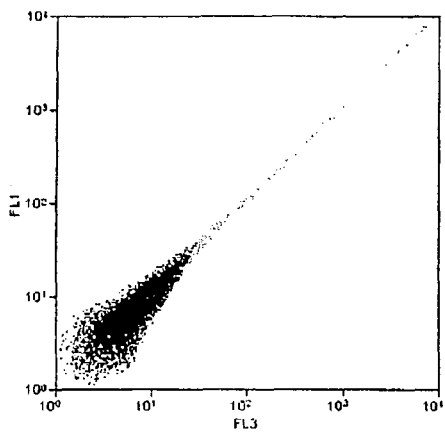
Figure 4:
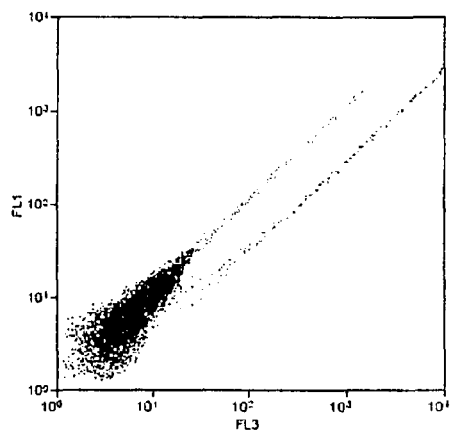
Figure 4:
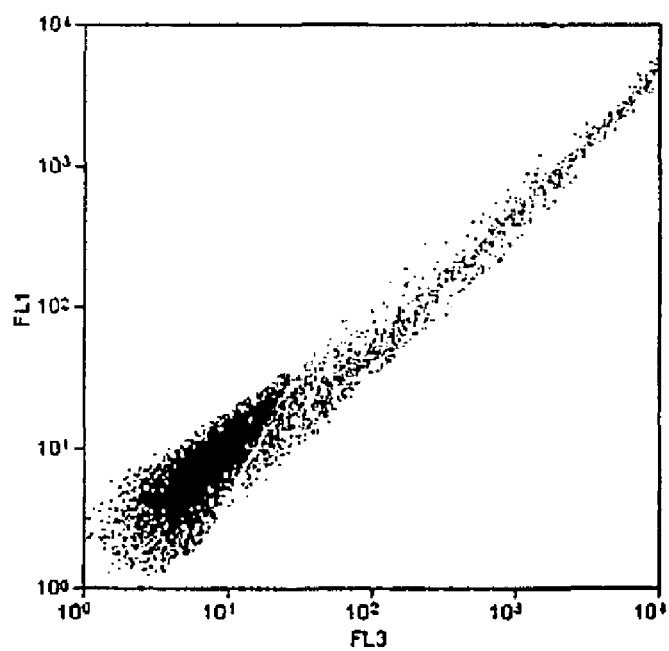
Figure 5:
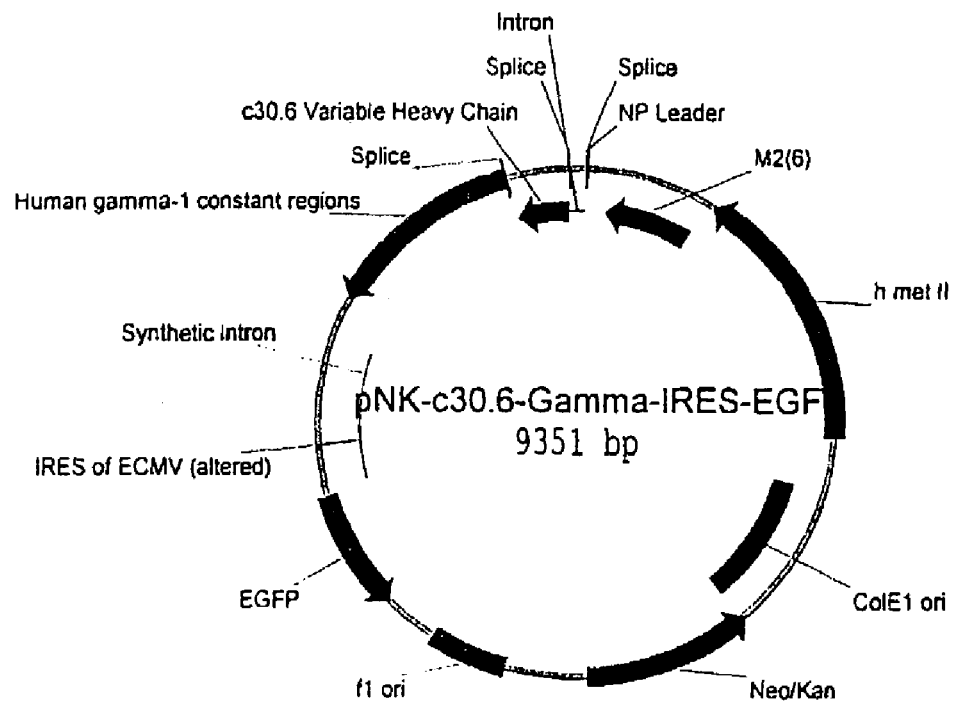
FIG. 5: pNK vectors. A: pNK-c30.6-Gamma-IRES-EGFP, B: pNK-c30.6-Kappa-IRES-EYFP.
Figure 5:
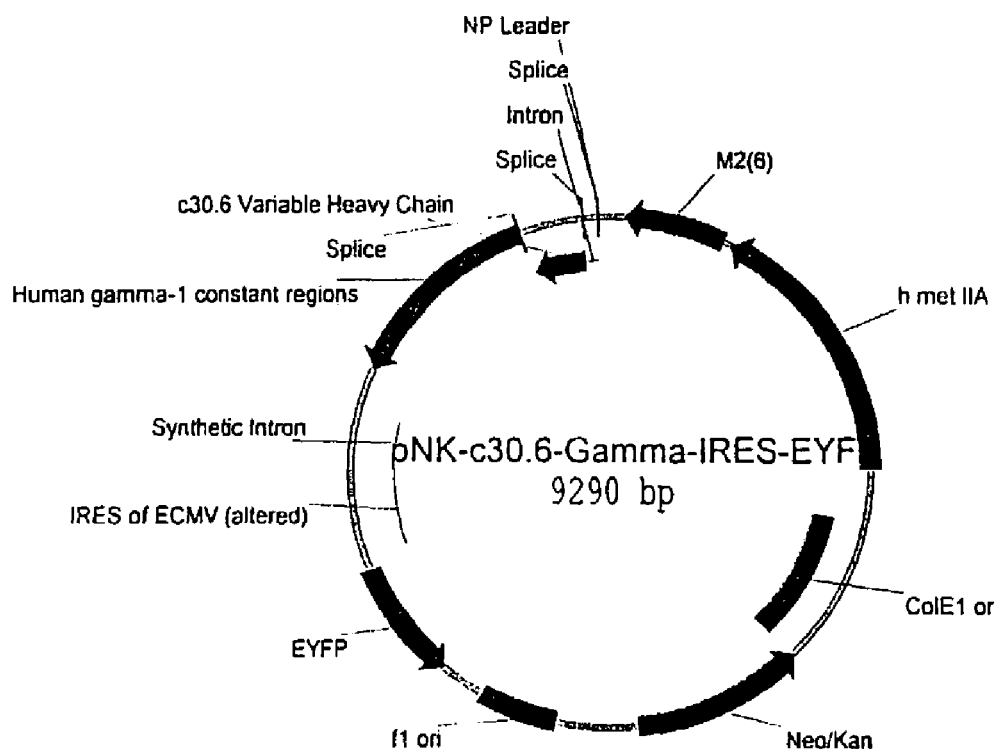

Due to the close proximity and overlap of the yellow and green fluorescent protein emission spectra, comparison of their signals is required to resolve them. Hence, it is possible to plot a graph on the flow cytometer with plotting FL3—green fluorescence against FL1—yellow fluorescence. Unlike the histograms above, every cell is represented by a single point. Where two or more cells are plotted at the same point, the colour of the region darkens. Along the abscissa increasing green fluorescence, as detected by the FL3 receptor, is plotted whilst along the ordinate yellow fluorescence, as detected by the FL1 receptor, is plotted. Thus, FIG. 4 shows the results of transfection experiments:

Firstly, as a control, CHO-K1 cells (not transformed) were submitted to FACS analysis. As shown in FIG. 4A (and in accordance with results shown in FIG. 1), these cells express low auto-fluorescence in both the FL1 and FL3 channels.

Secondly, CHO-K1 cells were transfected with the Clontech vector (pEGFP-C1 (carrying EGFP under the control of the CMV promoter) or pEYFP-C1 (carrying EYFP under the control of the CMV promoter). As shown in FIG. 4B cells transfected with pEGFP-C1 exhibit a distinct population with higher increasing fluorescence in the FL3 channel than in the FL1 channel. In contrast, and as shown in FIG. 4C, cells transfected with pEYFP-C1 exhibit a distinct population with higher increasing fluorescence in the FL1 channel than in the FL3 channel. The FACS profile generated by a mixture of these two transfected cell populations is shown in FIG. 4D. Both fluorescent cell populations occupy distinct regions on the profile.

Thirdly, CHO-K1 cells were co-tranfected with both vectors. The resulting FACS profile (FIG. 4E) shows that the co-transfected cells or a "dual" population occupies the region between the distinct green only and distinct yellow only populations. Hence, when tracking cells tranfected with the pNK antibody-IRES-fluorescent protein vectors, cells expressing both antibody chains can be identified by the fact that their fluorescence expression makes them fall within this "dual region" i.e the region between the green and yellow regions. Any transfection and/or selection/amplification procedure which can enrich the cell population within this dual region is likely to lead to higher expression of antibody. Furthermore any treatment, which moves the cells in this region further to the right (i.e. more green) and further up (i.e. more yellow) is likely to produce cells expressing antibody at higher levels.

The presence of the attenuated IRES offers the ability to select only those cells expressing the peptides or proteins of interest at a high level, without requiring high expression of the fluorescent protein markers. In addition, the FACS sorter is able to rapidly process many millions of cells which allows isolation of a reasonable number of these cells. Cells may be collected in pools of hundreds or thousands in 24 well plates or as individual clones in 96 or 384 well formats.

Modifications to the method described are also possible. Thus, for example, it may prove more powerful to first identify and isolate yellow fluorescing cells at a higher wavelength (e.g. 514 nm) at which less green fluorescence excitation occurs. Once these cells have been isolated they could be re-analysed for green fluorescence at 488 nm. Alternatively modifications of the wavelengths of the band pass filters should not be excluded from consideration.

The ability of the FACS machine to identify and isolate specific cell populations is also of use to allow the amounts of the two first cistron genes to be modified. Thus, within the "dual region", between the green only and yellow only populations, cells detected closer to the green only population, which express higher green than yellow fluorescence could be selected leading to isolation of cells with higher expression of one first cistron gene over the other first cistron gene.

Reculture of Cells and Analysis of Antibody Production

Once the cells have been sorted by the FACS machine and collected they may be returned to cell culture and propagated. The antibody producing ability of cells isolated in this manner is assayed using the appropriate ELISA or RIA protocol for the antibody of interest. Resulting pools or clones may be used for antibody production on various scales.

Using the pNK constructs described in the above examples, expression of c30.6 chimeric antibody was confirmed by a human region specific sandwich ELISA.

Isolation of Pools Enriched for Protein Expression

Figure 6:
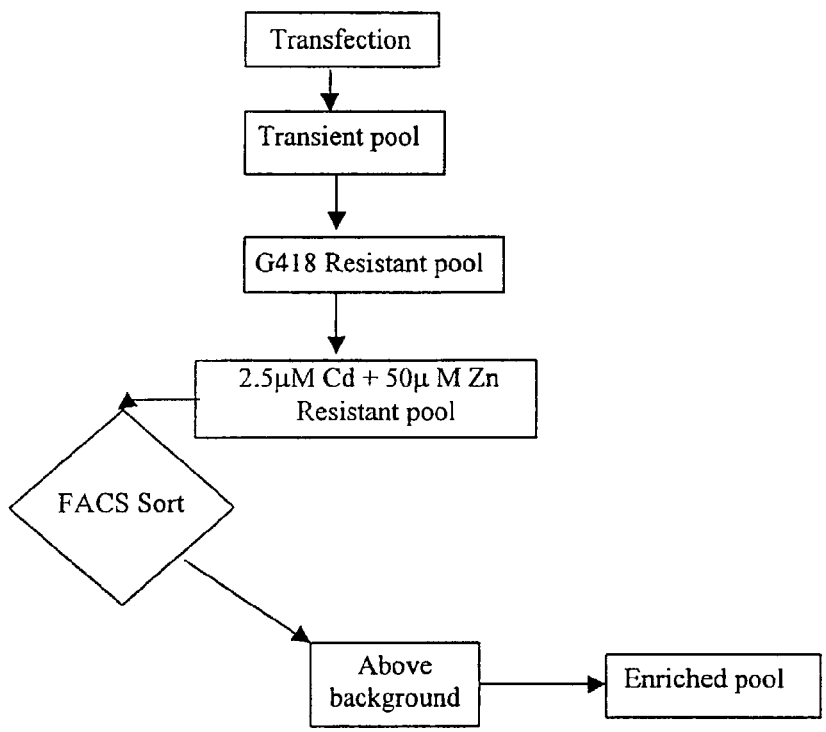
FIG. 6: A: A flow chart of the protocol used for the isolation of an enriched antibody expressing pool, B: FACS profile of 2.5 µM Cd+50 µM Zn resistant pool. Gated region from which cells were sorted is shown, C: FACS profile of resulting enriched antibody expressing pool.
Figure 6:
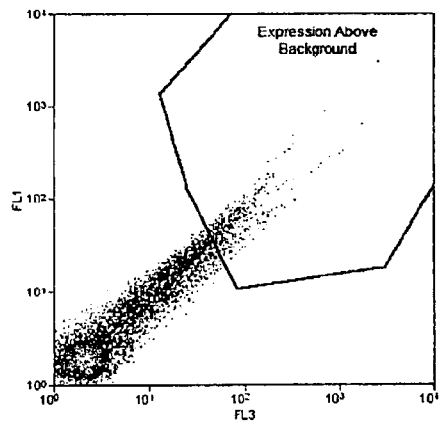
Figure 6:
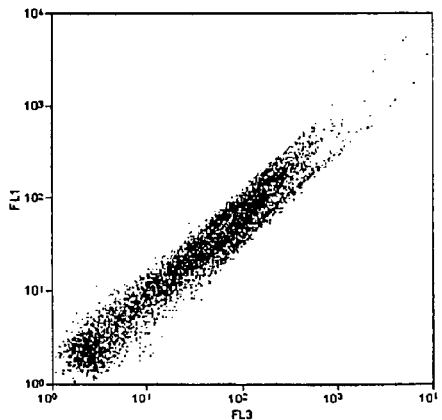

Following the methods described above, CHO-K1 cells were transfected with pNK-c30.6-Gamma-IRES-EGFP and pNK-c30.6-Kappa-IRES-EYFP expression vectors. The transfected cells were treated according to the protocol in FIG. 6A. Briefly following 14 days of selection in 400 µg/ml G418 a pool of resistant cells were obtained. These cells were then selected in 2.5 µM $CdCl_2$ and 50 µM $ZnSO_4$ for a further 14 days. After this second selection cells were submitted to FACS analysis as described. The resulting profile, FIG. 6B, shows that the vast majority of cells are fluorescing at levels below the second logarithmic decade of both the green (FL3) and yellow (FL1) channels. FIG. 6B also shows the gated area which was used to sort these cells, isolating only those found within the gated region. FACS of approximately $12 \times 10^6$ cells yielded 247,412 cells in this region. These cells were returned to culture and maintained under metal selection. After a further 14 days the resulting pool was reanalysed by FACS. FIG. 6C shows that the majority of the cells in the pool are now fluorescing at around the second log decade. Thus by application of two colour FACS sorting it is possible to increase the fluorescence level, for both fluorescent colours, to levels higher than those seen in the unsorted source pool. ELISA analysis of this enriched pool revealed that it produced antibody at a level 39 fold higher level than that of the unsorted pool. Thus by application of two colour FACS sorting it is possible to enrich a pool of antibody expressing cells, isolating a higher expressing pool.

Isolation of High Producing Clones

Figure 7:
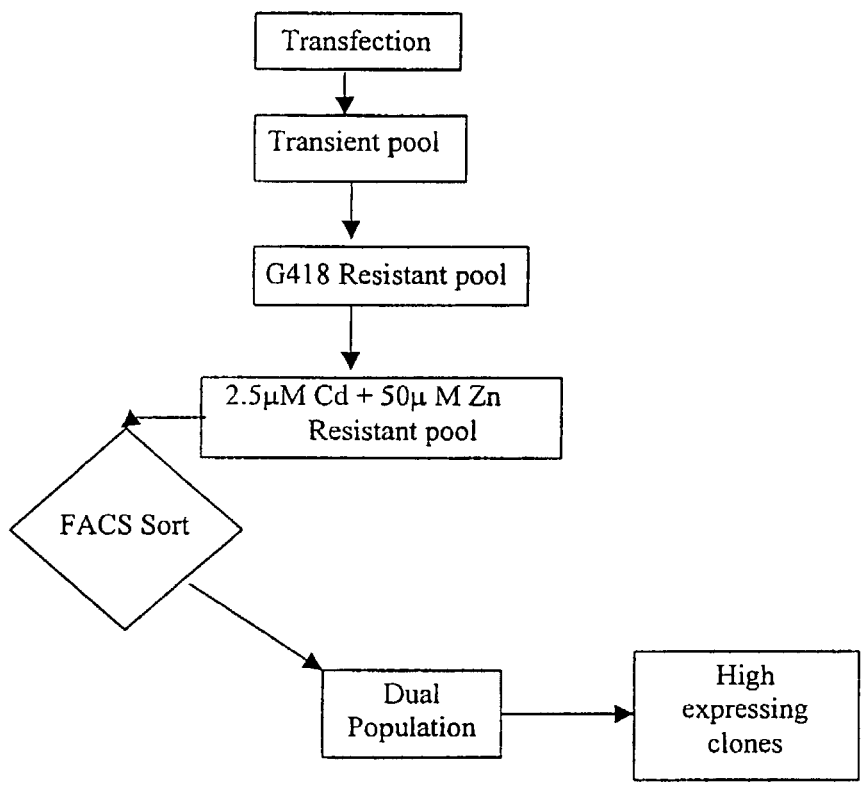
FIG. 7: A: Flow chart of the protocol used for the isolation of high expressing antibody clones, B: FACS profile of 2.5 µM Cd+50 µM Zn resistant pool. Gated region from which cells were sorted is shown, C: FACS profile of resulting enriched antibody expressing clone.
Figure 7:
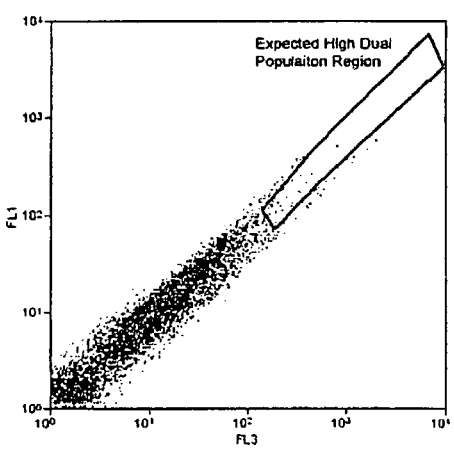
Figure 7:
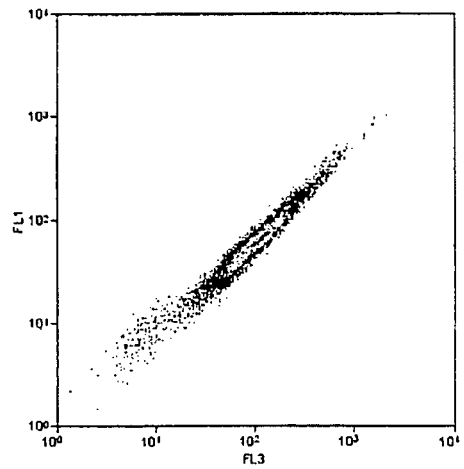

Following the methods described above, CHO-K1 cells were transfected with pNK-c30.6-Gamma-IRES-EGFP and pNK-c30.6-Kappa-IRES-EYFP expression vectors. The transfected cells were treated according to the protocol in FIG. 7A. Briefly following 14 days of selection in 400 µg/ml G418 a pool of resistant cells were obtained. These cells were then selected in 2.5 µM $CdCl_2$ and 50 µM $ZnSO_4$ for a further 14 days. After this second selection cells were submitted to FACS analysis as described. The resulting profile, FIG. 7B, shows that the vast majority of cells are fluorescing at levels below the second logarithmic decade of both the green (FL3) and yellow (FL1) channels. FIG. 7B also shows the gated area which was used to sort these cells, isolating only those found within the dual population region. Thus the cells found in this gate express both of the dicistronic constructs at high levels. FACS of approximately $5 \times 10^6$ cells yielded 20 wells of a 96 well plate with one cell per well. These cells were returned to culture and maintained under metal selection. After a further 28 days, the extra 14 days allows the clone to grow up from one cell, the resulting clone was re-analysed by FACS. FIG. 7C shows that all of the cells in the clone are now fluorescing at around the second log decade. All the cells within this region exhibit higher fluorescence and were derived from a single sorted cell. Thus by application of two colour FACS sorting it is possible to increase the fluorescence level, for both fluorescent colours, to levels higher than those seen in the unsorted source pool. It is also possible to isolate single cells whose progeny maintain similar levels of fluorescence. ELISA analysis of this clone revealed that it produced antibody at a level 50 fold higher level than that of the unsorted pool. Thus by application of two colour FACS sorting it is possible to isolate a clone of antibody expressing cells, which expresses antibody at greatly increased levels.

It will be clear to the skilled addressee that it is possible to isolate cells expressing the fluorescent proteins in predetermined ratios. In particular, it would be well within the capacity of one skilled in the art to identify cells which express the fluorescent proteins in, for example, a ratio of about 1:1 by determining the intensity of the fluorescent signals relative to one another. Since the expression of the fluorescent proteins is a means by which to infer the level of expression of the peptides or proteins of interest, clearly it would be possible to select cells expressing the peptides or proteins of interest in desired ratios using ratios of fluorescence intensity values. This is of particular significance in the production of bi- or multi-subunit proteins such as, for example, the production of antibodies where cells expressing a specific ratio of heavy to light chains can be selected.

It will also be clear to the skilled addressee from the above that standard laboratory techniques (for example, Sambrook et al., 1989) can be utilised to isolate the antibody, peptide or protein of interest from the cells.

Although the invention has been described with reference to specific examples, it will be appreciated by those skilled in the art that the invention may be embodied in many other forms.

REFERENCES

1. Bailey C G, Baig M, Gray P P and Sunstrom N A. A rapid selection/amplification procedure for high-level expression of recombinant protein in a metal-amplifiable mammalian expression system. Biotechnology Techniques 1999 13: 615-619.
2. Chalfie M, Tu Y, Euskirchen G, Ward W W, Prasher D C. Green fluorescent protein as a marker for gene expression. Science 1994 263(5148): 802-5.
3. Haas J, Park E C, Seed B. Codon usage limitation in the expression of HIV-1 envelope glycoprotein. Curr Biol 1996 6(3): 315-24.
4. Lybarger L. Dempsey D, Patterson G H. Piston D W, Kain S R, Chervenak R. Dual-color flow cytometric detection of fluorescent proteins using single-laser (488-nm) excitation. Cytometry 1998 31(3):147-52.
5. Martinez-Salas, E. Internal ribosome entry site biology and its use in expression vectors. Current Opinion in Biotechnology (1999) 10:458-464.
6. McNeall J, Sanchez A, Gray P P, Chesterman C N, Sleigh M. T. Hyperinducible gene expression from a metallothionein promoter containing additional metal-responsive elements. Gene (1989) 76:81-88.
7. Mount P F, Sutton V R, Li W, Burgess I, McKenzie I F, Pietersz G A, Trapani J A. Chimeric (mouse/human) anti-colon cancer antibody c30.6 inhibits the growth of human colorectal cancer xenografts in scid/scid mice. Cancer Research (1994) 23:6160-6166.
8. Mountford, PS, and Smith, AG. Internal ribosome entry sites and dicistronic RNAs in mammalian transgenesis. Trends in Genetics (1995) 11:179-184.
9. Ormo M. Cubitt A B, Kallio K, Gross L A, Tsien R Y, Remington S J. Crystal structure of the *Aequorea victoria* green fluorescent protein. Science 1996 273(5280): 1392.
10. Pak, S C O, Hunt, S M N, Bridges, M W Sleigh, M J, Gray, P P 1996 Super-CHO—A cell line capable of autocrine growth under fully defined protein-free conditions. Cytotechnol. 22: 139-146.
11. Rees S, Coote J, Stables J, Goodson S, Harris S, Lee M G. Bicistronic vector for the creation of stable mammalian cell lines that predispose all antibiotic-resistant cells to express recombinant protein. Biotechniques 1996 20(1): 102-104.
12. Sambrook, J., Fritsch, E. and Maniatis, T. Molecular Cloning: A Laboratory Manual, $2^{nd}$ Ed., Cold Spring Harbor Laboratory Press, Cold Spring Harbor, N.Y. (1989).
12. Yang T T. Sinai P. Green G, Kitts P A, Chen Y T, Lybarger L, Chervenak R, Patterson G H, Piston D W, Kain S R. Improved fluorescence and dual color detection with enhanced blue and green variants of the green fluorescent protein. J Biol Chem 1998 273(14):8212-6.

The claims defining the invention are as follows:
1. An in vitro method of screening transformed or transfected cells to identify those cells expressing simultaneously and/or sequentially at least two peptides or proteins of interest in predetermined ratios, including:
    (a) transforming or transfecting cells with at least two expression cassettes, wherein each expression cassette includes a gene encoding a peptide or a protein of interest linked at its 3' end to an attenuated internal ribosome entry sequence (IRES) wherein the attenuated IRES is linked at its 3' end to a fluorescent marker gene, such that the genes and their respective attenuated IRESs are in the same orientation, and wherein the detectable fluorescence of the products of the marker genes attached to each attenuated IRES are different; and wherein at least one of the attenuated IRESs is selected such that the fluorescent marker gene to which it is linked is expressed less than the peptide or protein of interest to which it is linked;
    (b) expressing the genes encoding the peptides or proteins of interest such that expression of the genes encoding the peptides or proteins of interest results in expression of the fluorescent marker genes;
    (c) identifying cells expressing at least two peptides or proteins of interest in predetermined ratios by detecting fluorescent signals from the products of the marker genes in the transformed or transfected cells using a fluorescence detection means.

2. The method according to claim 1, wherein transforming or transfecting comprises transforming or transfecting more than two expression cassettes into the cells.
3. The method according to claim 1, further comprising selecting and isolating the cells identified on the basis of their expression of the fluorescent marker genes from other cells.
4. The method according to claim 3, further comprising culturing the isolated cells and/or subjecting the isolated cells to further selection procedures.
5. The method according to any one of claims 1 to 4, wherein transforming or transfecting of the expression cassettes is performed sequentially.
6. The method according to claim 1 wherein the fluorescent marker genes encode enhanced green fluorescent protein (EGFP), enhanced yellow fluorescent protein (EYFP), blue fluorescent protein (BFP), enhanced blue fluorescent protein (EBFP), enhanced cyan fluorescent protein (ECFP), dsRed or an analogue thereof.
7. The method according to claim 1 wherein the fluorescent marker genes encode EGFP and EYFP respectively.
8. The method according to claim 1 wherein the detection means is a fluorescence assisted cell sorter (FACS).
9. The method according to claim 8, further comprising gating and isolating from other cells expressing at least two peptides or proteins of interest.
10. The method according to claim 1 wherein the detection means is a fluorescent plate reader, laser scanning cytometer or a microscope designed to allow visualisation of fluorescent cells.
11. The method according to claim 1 wherein the genes encoding the peptides or proteins of interest are genes encoding peptides which are subunits of a single protein.
12. The method according to claim 11 wherein the peptides of interest are the heavy and light chains of an antibody.
13. The method according to claim 1 wherein the proteins of interest are Insulin-like Growth Factor I (IGF-1) and transferrin.
14. The method according to claim 1 wherein at least two of the peptides or proteins of interest are expressed in a ratio of about 1:1.
15. The method according to claim 1 wherein at least one of the peptides or proteins of interest is expressed at a different level to the other or others.
16. The method according to claim 1 wherein at least one of the peptides is a limiting subunit of a bi- or multi-unit molecule.
17. The method according to claim 16 wherein the limiting subunit is expressed at equivalent or higher levels than one or more of the other peptides of interest.
18. The method according to claim 1 wherein at least one of the expression cassettes further includes a gene allowing selection in growth medium.
19. The method according to claim 18 wherein the gene allowing selection in growth medium is a gene encoding a peptide or protein that confers metal resistance or resistance to an antibiotic.
20. The method according to claim 19 wherein the metal resistance is resistance to cadmium and/or zinc.
21. The method according to claim 20 wherein the gene encoding metal resistance is the human metallothionein gene.
22. The method according to claim 19 wherein the gene encoding antibiotic resistance is a gene encoding resistance to geneticin (G418).
23. The method according to claim 1 wherein at least one of the expression cassettes is under metal inducible control.
24. The method according to claim 23 wherein the metal inducible control is achieved by means of the M2.6 promoter.

25. The method according to claim 1 wherein at least one of the expression cassettes is a linear fragment of DNA.

26. The method according to claim 1 wherein at least two of the expression cassettes are on the same DNA fragment.

27. The method according to claim 1 wherein at least one of the expression cassettes is included in a vector.

28. The method according to claim 27 wherein the vector is an episomal plasmid.

29. The method according to claim 1 wherein at least one of the expression cassettes is integrated into the cell's genomic DNA.

30. The method according to claim 1 wherein the cells transformed or transfected are mammalian cells.

31. The method according to claim 30 wherein the cells transformed or transfected are chinese hamster ovary (CHO) cells.

32. The method according to claim 31 wherein the cells are CHO-K1 cells.

33. The method according to claim 1 wherein the cells transiently express at least one of the peptides or proteins of interest.

34. The method according to claim 1 wherein the cells stably express at least one of the peptides or proteins of interest.

35. The method according to claim 1, wherein identifying the cells is performed after 2 to 40 days' incubation post transformation or transfection.

36. The method according to claim 35 wherein identifying the cells is performed after about 28 days' selection in one or more selective growth media.

37. The method according to claim 36 wherein identifying the cells is performed after about 14 days' selection in a first selective growth medium and about 14 days' selection in a second selective growth medium.

38. The method according to claim 37 wherein the first selective growth medium includes geneticin to select for cells having geneticin resistance and the second growth medium includes metal salts to select for cells having a gene encoding metal resistance, and the genes encoding resistance are on the expression cassettes.

39. A method of producing a peptide or protein of interest comprising:
   (a) identifying cells producing the peptide or protein according to the method of claim 1; and
   (b) producing the peptide or protein from the identified cells.

40. A method of screening transformed or transfected cells to identify those cells expressing simultaneously and/or sequentially at least two peptides or proteins of interest in predetermined ratios, including:
   (a) transforming or transfecting cells with a first expression cassette including a gene encoding one peptide or protein of interest linked at its 3' end to an attenuated IRES, the attenuated IRES being linked at its 3' end to an enhanced green fluorescent protein (EGFP) marker gene, wherein the gene encoding the peptide or protein of interest, the attenuated IRES and the EGFP marker gene are in the same orientation, wherein the EGFP marker gene is expressed at a lower level than the peptide or protein of interest;
   (b) transforming the same cells with a second expression cassette including a gene encoding one peptide or protein of interest linked at its 3' end to attenuated IRES, the IRES being linked at its 3' end to an enhanced yellow fluorescent protein (EYFP) marker gene, wherein the gene encoding the peptide or protein of interest, the attenuated IRES and the EYFP marker gene are in the same orientation, wherein the EYFP marker gene is expressed at a lower level than the peptide or protein of interest;
   (c) expressing the genes encoding the peptides or proteins of interest such that expression of the genes encoding the peptides or proteins of interest results in expression of the EGFP and EYFP marker genes; and
   (d) identifying cells expressing at least two peptides or proteins of interest by detecting the presence of EGFP and EYFP in the transformed or transfected cells using FACS analysis.

* * * * *